(12) United States Patent
Tardif et al.

(10) Patent No.: US 7,863,584 B2
(45) Date of Patent: Jan. 4, 2011

(54) OPTICAL CODING DEVICE BY PLASMON EFFECT AND AUTHENTICATION METHOD USING THE DEVICE

(75) Inventors: Francois Tardif, Lans En Vercors (FR); Olivier Raccurt, Chelieu (FR); Céline Noel, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 11/980,936

(22) Filed: Oct. 31, 2007

(65) Prior Publication Data

US 2008/0149850 A1    Jun. 26, 2008

(30) Foreign Application Priority Data

Dec. 22, 2006  (FR) ................................. 06 55888

(51) Int. Cl.
*G01J 1/58*    (2006.01)
(52) U.S. Cl. ............... 250/458.1; 250/361 R; 250/461.1; 250/483.1; 250/271; 250/459.1; 356/71; 506/41
(58) Field of Classification Search ............ 250/361 R, 250/362, 365, 367, 372, 458.1, 459.1, 461.1, 250/483.1, 271; 356/71; 427/7; 436/56; 506/41
See application file for complete search history.

(56) References Cited

U.S. PATENT DOCUMENTS

| | | | |
|---|---|---|---|
| 4,146,792 A | | 3/1979 | Stenzel et al. |
| 5,866,433 A | * | 2/1999 | Schalkhammer et al. .... 436/525 |
| 6,514,767 B1 | * | 2/2003 | Natan .......................... 436/166 |
| 6,946,785 B2 | * | 9/2005 | Ito et al. ..................... 313/461 |
| 2003/0166297 A1 | * | 9/2003 | Natan .......................... 436/166 |
| 2003/0228682 A1 | * | 12/2003 | Lakowicz et al. ........ 435/287.2 |
| 2004/0157237 A1 | | 8/2004 | Malak et al. |
| 2004/0233465 A1 | * | 11/2004 | Coyle et al. .................. 358/1.9 |
| 2005/0142605 A1 | | 6/2005 | Malak |
| 2005/0164169 A1 | * | 7/2005 | Malak ............................. 435/5 |
| 2005/0214536 A1 | * | 9/2005 | Schrier et al. ............... 428/403 |
| 2006/0141268 A1 | * | 6/2006 | Kalkan et al. ............... 428/446 |
| 2006/0183246 A1 | * | 8/2006 | Wiesner et al. ............. 436/524 |
| 2007/0164377 A1 | * | 7/2007 | Gruhlke et al. ............. 257/414 |
| 2007/0166761 A1 | * | 7/2007 | Moore ......................... 435/7.1 |
| 2007/0243382 A1 | * | 10/2007 | Chan et al. .................. 428/403 |
| 2008/0241262 A1 | * | 10/2008 | Lee et al. .................... 424/490 |
| 2009/0022766 A1 | * | 1/2009 | Geddes ........................ 424/401 |
| 2009/0140206 A1 | * | 6/2009 | Nie et al. ............... 252/301.16 |

OTHER PUBLICATIONS

Schaadt, et al. "Enhanced semiconductor optical absorption via surface plasmon excitation in metal nanoparticles", Applied Physics Letters 86, 063106, published Feb. 2, 2005.*

Hutter et al. "Exploitation of Localized Surface Plasmon Resonance", Advanced Materials, vol. 16, No. 19, published Oct. 4, 2004; pp. 1685-1706.*

Tanaka et al., "Luminescence Enhancement of Ruthenium Complexes in Polymer Nanosheet by Surface Plasmon Resonance of Metal Nanoparticle." Chemistry Letters vol. 34, No. 9, Published Aug. 6, 2005 (received from the internet http://www.jstage.jst.go.jp/article/cl/34/9/1246/_pdf) [Retrieved on Apr. 9, 2010].*

Gaponenko, "Modification of Spontaneous Emission and Scattering of Light in Nanostructures." Proceedings of the Symposium on Photonics Technologies for the 7th Framework Program, Wroclaw Oct. 12-14, 2006; (received from the internet: http://www.opera2015.org/deliverables/D_4_3_Wroclaw_Symposium/articles/27_Gaponenko.pdf)_ [Retrieved on Apr. 4, 2010].*

* cited by examiner

*Primary Examiner*—David P Porta
*Assistant Examiner*—Yara B Green
(74) *Attorney, Agent, or Firm*—Burr & Brown

(57) ABSTRACT

This optical coding device comprises a plurality of aggregates suitable for emitting infrared, visible or ultraviolet rays by luminescence, at least one of the said aggregates comprising at least one luminophore. This aggregate further comprises at least one particle consisting of a surface plasmon effect material, the said luminophore and the said particle being suitable for entering into interaction.

21 Claims, 2 Drawing Sheets

OPTICAL CODING DEVICE BY PLASMON EFFECT AND AUTHENTICATION METHOD USING THE DEVICE

FIELD OF THE INVENTION

The present invention relates to an optical coding device comprising a plurality of aggregates, capable of emitting by luminescence in the infrared, visible and/or ultraviolet ranges. This aptitude for luminescence is due to the presence of one or more luminophores in these aggregates.

The optical coding device covered by the present invention therefore relates to the field of product authentication and traceability, for example in connection with the detection of counterfeits or fakes.

BACKGROUND OF THE INVENTION

Various technical means are known today for tracking and authenticating a product. This product may be an art object, a commercial consumer product, an identity document, a means of payment, etc.

Such a product may therefore consist of one or more materials, which include for example, paper, textile, leather, plastic, etc. Among the means employed today to trace and authenticate such products, mention can be made of the barcode, holograms which must be decoded optically, electronic labels (sometimes denoted by the acronym RFID for "Radio Frequency Identification Data") which are decoded by an electromagnetic method. Also known are cryptography techniques which consist in attributing an encrypted numerical code to the product to be authenticated, or the insertion of specific elements such as tracers (luminescent, magnetic, chemical, etc.) in the very structure of the object or the product to be authenticated.

The present invention relates to the latter field and, more particularly, the method for tracing or authenticating a product by means of luminescent tracers.

In a manner known per se, such luminescent tracers form an optical code which must be read in order to authenticate the object or product. In general, a mixture is applied comprising one or more luminophores, that is small grains, molecules or particles of light emitting material, directly to the surface of the product to be authenticated.

During the authentication of the product, an external luminescent source is used to excite the luminophores thus deposited, and the light rays that they re-emit by deexcitation are collected. The analysis of the luminous spectra re-emitted by these luminophores serves accurately to determine the optical code which has been attributed to the object to be authenticated associated with these luminophores.

Document U.S. Pat. No. 4,146,792 provides an example of such an optical coding designed to authenticate fiduciary instruments. In a manner known per se, the electrons of the atoms of the luminophore are excited by the photons of a light source, and then, during their deexcitation, emit photons whereof the wavelength depends on that of the incident rays. In this case, the fluorescence spectrum emitted by the luminophore is partially absorbed by a dye, so that a purely photon mechanism is involved. It is therefore difficult to authenticate the nature of such luminophores. Thus, the authentication of the fiduciary instrument is much more reliable.

However, luminophores designed for such authentication applications must have a high luminescence yield (defined as the ratio of the number of photons emitted to the number of photons absorbed by the luminescent material) and must be sufficiently robust to be durably able to emit by luminescence.

In fact, luminophores having these yield and robustness properties exist in limited numbers, so that the possible combinations for forming optical codes are also limited in number. Insofar as the fluorescence spectra, particularly the peaks, are already known and listed, it is then relatively easy to identify the luminescent materials making up the luminophores used, and thereby to counterfeit the optical code.

Moreover, in the rare cases in which the luminescent material employed is relatively unknown, it is relatively easy to analyse the physicochemical spectrum of the material comprising the luminophores. This makes it possible to fake the optical coding device and thereby falsify authentic objects.

Document US 2005/142605 describes the use of nanoparticles having a surface plasmon effect, to increase the absorption or fluorescence properties of chemical substances intended for marking a medium. Thus, it is possible to apply a lower excitation to light sensitive materials.

It is therefore an object of the present invention to provide an optical coding device that is unfalsifiable and unique. This optical coding device has the basic purpose of avoiding the drawbacks of the prior art, and particularly of preventing the retrospective analysis of the luminous spectrum re-emitted by the luminescent aggregates associated with the object to be authenticated.

SUMMARY OF THE INVENTION

The present invention therefore relates to a reliable optical coding device, difficult to decode and virtually impossible to infringe.

This optical coding device comprises a plurality of aggregates suitable for emitting infrared, visible or ultraviolet rays by luminescence, at least one of the said aggregates comprising at least one luminophore, and further comprises at least one particle consisting of a surface plasmon effect material, the said luminophore and the said particle being suitable for entering into interaction.

In other words, the optical coding device covered by the present invention comprises two types of elements aggregated together and interacting during the emission of luminescence by one of them.

The said particle is suitable for presenting a surface plasmon effect when it is extracted by means of an energy with a spectrum entirely or partially covering the emission spectrum of the said luminophore.

In the context of the present invention, the expression surface plasmon effect means the collective excitation of the electrons located on the conduction balance of the atoms making up the said particle. The particle must be excited by energies comprised within the energy spectrum of the luminophore.

It is thereby possible to obtain a significant interaction and accordingly to modulate the luminous spectrum emitted to authenticate the object provided with such an optical coding device.

In the context of the invention, the expression "modulate the luminous spectrum" means the ability to selectively increase or decrease certain parts of the optical signature (emission or absorption) of the luminophore, thanks to the presence of a surface plasmon effect particle.

The modification of the spectral signature of the luminophore depends in particular:
on the distance between the surface plasmon effect particle and the luminophore;
on the plasmon resonance frequencies, adjustable for example thanks to the dimension of the plasmon particle, compared with those of the luminophore.

Thus, this combination brings about this modification and the control of the various parameters affecting this modification considerably increase the number of unique optical signatures available.

According to another feature of the invention, the aggregate is formed by an envelope encapsulating the said luminophore and the said particle. Advantageously, this envelope consists of a material transparent to infrared, visible or ultraviolet rays.

In doing so, the luminophore and the particle are "embedded" and "coated" in this envelope, the aggregate having the form of beads.

The combination of the luminophore and the particle in the same physical entity, which may be called "coding particle", have significant advantages:

this coding entity can be fabricated extemporaneously, independently from the medium to be marked. At the time of marking, it suffices to deposit or integrate it with the said medium. Such a luminophore/surface plasmon effect particle combination can therefore be used for marking materials as different as paper, glass, plastics, etc.;

the coexistence of the luminophore and the surface plasmon effect particle in a physical entity having a predefined and stable structure serves optimally to control the interaction between these two molecules, particularly their distance, which plays a crucial role in the modification of the spectrum.

Advantageously, this aggregate has a dimension smaller than 200 nm.

Such a dimension serves to prepare relatively small aggregates which do not alter the mechanical properties of fine materials (particularly films and/or fibres) components of the object to be authenticated. In fact, optical coding devices having an excessive size risk not tolerating the mechanical properties and hence locally damaging the object to be authenticated.

Furthermore, in the case in which the optical coding device has dimensions smaller than 60 nm, it is undetectable by the naked eye.

Moreover, this dimension, advantageously smaller than 200 nm, is perfectly compatible with short-distance interactions between luminophores and plasmon effect particles.

In fact and according to one advantageous feature of the invention, the distance between the luminophore and the particle having a surface plasmon effect is shorter than 30 nm. Such a distance favours the interaction between the particle and luminophore.

This distance may even be reduced to nil, the luminophore and the said particle being in contact.

According to another feature of the invention, the luminophore or the said particle is covered by a separating layer, came from a material transparent to the said infrared, visible or ultraviolet rays.

In other words, a material called spacer is inserted between the luminophore and the particle, serving to establish a distance between them that is favourable to this interaction.

According to the invention, the surface plasmon effect particles comprise an electrically conducting metal having a high density and a high electronic mobility, selected from the group comprising gold, silver, copper, aluminium and sodium.

Such metals can in fact generate surface plasmons when their atoms are excited in the infrared, visible or ultraviolet ranges.

Alternately, the said particles may comprise a nanoparticle made from a dielectric or semiconductor material covered by an electrically conducting metal film having a high density and a high electronic mobility, selected from the group comprising gold, silver, copper, in order to form an optical resonator suitable for presenting a surface plasmon effect suitable for the luminescence spectrum of the said luminophore.

Such a particle therefore serves to generate surface plasmons by optical resonance to match the emission spectra of the luminophores. The number of possibility luminescences can thereby be increased by modifying the dimension of these particles or the thickness of the optical resonator film made of such particles.

Such materials thereby serve to prepare efficient optical resonators.

The use of an optical resonator nanodevice for the plasmon effect, that is, a layer of metal on an insulating particle, is particularly preferred. In fact, this alternative serves to obtain much wider resonance frequencies than in the case of single plasmon nanoparticles: typically several hundreds of nm of the visible to the IR ranges, for example, by modifying only the geometric dimensions of the resonator. This makes it unnecessary to modify its chemical nature to change the plasmon frequency.

According to the invention, the luminophore is selected from:

organic luminophores selected from the group comprising rhodamine-B-isothiocyanate (RBITC), fluorescein isothiocyanate (FITC), fluorescein, rhodamine, eosine, pyranine, aminoG;

nanocrystals of ZnO, ZnS, CdSe, InGaP, InP, Si, Ge, GaAs, GaP, GaAsP;

oxide, sulphide, phosphate or vanadate matrices doped with a rare earth ion, such as $Y_2O_3$:Eu, $Y_2O_2S$:Eu, $BaMgAl_{16}O_{17}$:Eu, $GdBO_3$:Eu, $YGdBO_3$:Eu, $YPVO_4$:Eu, $Gd_2O_3$:Tb, $Gd_2O_2S$:Tb, $Y_3Al_5O_{12}$:Tb, $Y_2SiO_5$:Ce, $LaPO_4$:Tb, Ce;

semiconductor or oxide matrices doped with a transition metal, such as ZnS:Mn, ZnS:Au, ZnS:Al, ZnS:Ag, ZnO:Ag, ZnO:Cu, ZnO:Mn, $Zn_2SiO_4$:Mn, $Al_2O_3$:Cr, $Al_2O_3$:Ti Such a luminophore is suitable for emitting infrared, visible or ultraviolet rays by luminescence.

According to the invention, the separating layer covering the luminophore and/or the surface plasmon effect particles consists of a polymer or an inorganic oxide such as polysiloxane ($SiO_2$), zirconium oxide ($ZrO_2$) or alumina ($Al_2O_3$).

Such a separating layer is transparent to infrared, visible or ultraviolet rays and it serves to control the distance between the luminophores and the particles.

According to the invention, the envelope encapsulating the luminophore and the surface plasmon effect particles consists of an inorganic oxide such as polysiloxane ($SiO_2$), zirconium oxide ($ZrO_2$) or alumina ($Al_2O_3$).

Such an envelope is transparent to infrared, visible or ultraviolet rays and serves to control the distance between the luminophore and the said particles.

The invention also relates to a method for marking an object, particularly consisting of a textile, paper, glass or plastic, in order to make it unfalsifiable. This method consists in joining to said object an optical coding device as previously described.

The invention finally relates to a method for authenticating such an object. It comprises the steps consisting:

illuminating the said object using a light source emitting infrared, visible or ultraviolet rays;

sensing the rays re-emitted by the said object using a spectral detector;

comparing the luminous spectrum emitted by the said object to a reference spectrum;

declaring the authenticity or inauthenticity of the said object.

BRIEF DESCRIPTION OF THE DRAWINGS

The manner in which the invention can be implemented and the advantages it provides will also appear from the exemplary embodiments described below, provided for information and non-limiting, in conjunction with the figures appended to in which.

To simplify the reading of these figures, the luminophore surfaces are shown by black areas, the surface of the surface plasmon effect particles is shown by white areas containing black dots, the surfaces of the separating layers are shown by oblique cross hatching, while the surfaces of the encapsulating envelopes are shown by white areas.

This is why the unit elements in FIGS. 1 to 5 are not individually numbered, thereby making it possible to present clear figures.

DETAILED DESCRIPTION OF THE INVENTION

Figure 1:
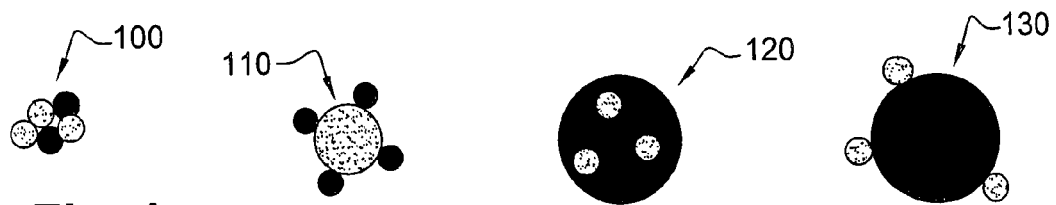
FIG. 1 is a schematic representation of a cross section of four alternatives according to a first embodiment of the invention.

FIG. 1 shows four alternative embodiments according to the first embodiment of the invention. The four aggregates 100, 110, 120 and 130 shown here all consist of luminophores aggregated with surface plasmon effect particles.

As may be observed, the dimensions and respective positions of the luminophores and the particles may vary from one embodiment to another. Thus, the aggregate 100 comprises two joined luminophores, for example joined by van der waals forces, having three surface plasmon effect particles. In the case of the aggregate 100, the luminophores and the particles have similar dimensions.

Conversely, the aggregate 110 comprises a large surface plasmon effect particle on which four luminophores are aggregated (at least in the plane of the sheet constituting the cross section plane of this aggregate).

The aggregate 130 corresponds to the reverse situation of the aggregate 110, where three small particles are associated with one "large" luminophore.

The aggregate 120 is a different and original structure, because the surface plasmon effect particles are accommodated directly within a large luminophore.

Insofar as the luminophores and the particles making up the aggregates 100, 110, 120 and 130 are in contact with one another, that is that they are separated by a zero distance, they are able to enter into interaction when subjected to infrared, visible or ultraviolet rays emitted by a light source, for example during the authentication of an object. The luminophores then re-emit a characteristic luminous spectrum which is modulated by the interactions with the surface plasmon effect particles. Such a modulation is described below in conjunction with FIG. 6.

Figure 2:
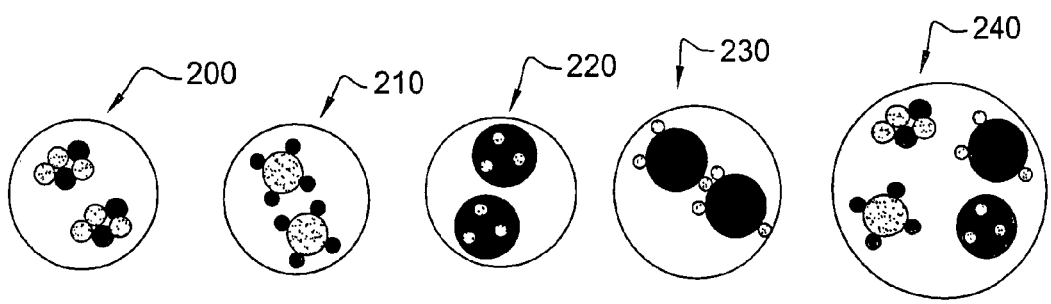
FIG. 2 is a schematic representation of a cross section of five alternatives according to a second embodiment of the invention.

FIG. 2 shows five alternative embodiments according to the second embodiment of the invention. The five aggregates 200, 210, 220, 230 and 240 all comprise luminophores combined with surface plasmon effect particles. The whole, being encapsulated or embedded within an envelope made from a material transparent to infrared, visible or ultraviolet rays. As may be observed in FIG. 2, the clusters encapsulated by the envelopes are identical to the aggregates 100, 110, 120 and 130 shown in FIG. 1. Thus, the aggregate 200 comprises two identical combinations to the aggregate 100, embedded in an envelope. Similarly, the aggregate 210 comprises two identical combinations to the aggregate 110, embedded in an envelope, and so on.

The aggregate 240 comprises an envelope encapsulating four combinations identical respectively to the aggregates 100, 110, 120 and 130.

In consequence, just as each aggregate 100, 110, 120 and 130 in FIG. 1 is capable of constituting an optical coding device having a unique, hence unfalsifiable luminous spectrum, the aggregates 200, 210, 220, 230 and 240 are capable of constituting a unique and unfalsifiable optical coding device.

Figure 3:
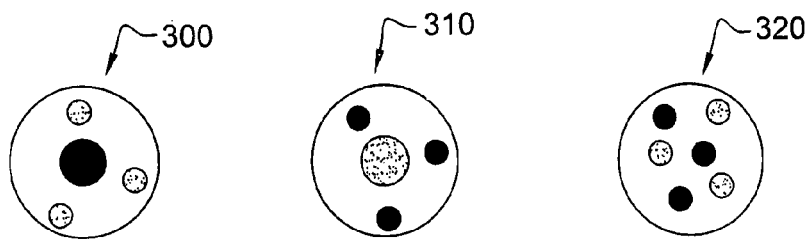
FIG. 3 is a schematic representation of a cross section of three alternatives according to a third embodiment of the invention.

FIG. 3 corresponds to a third embodiment of the invention, in which the aggregates, 300, 310 and 320 all consist of one or more luminophores, one or more surface plasmon effect particles, the whole being encapsulated by an envelope similar to the one making up the aggregates 200, 210, 220, 230 and 240 in FIG. 2.

However, in the case of FIG. 3, the luminophores and the particles are isolated within each envelope.

According to the invention, the distance between a luminophore and a particle is shorter than a few tens of nanometers, preferably to 30 nm. As already stated above, this distance enables the particles and the luminophores to interact in order to modulate the luminous spectrum re-emitted by luminescence. To control this distance or interval between luminophores and particles, it is desirable to control the relative proportions of luminophores, particles and material making up this envelope during their blending.

As in the case in FIG. 1, the component elements of the aggregates 300, 310 and 320 in FIG. 3 have various respective dimensions and positions. Thus, the aggregate 300 comprises a "large" luminophore and three small particles, while the aggregate 310 has an "antisymmetrical" structure and the aggregate 320 has a luminophore and particles of similar dimensions.

Figure 4:
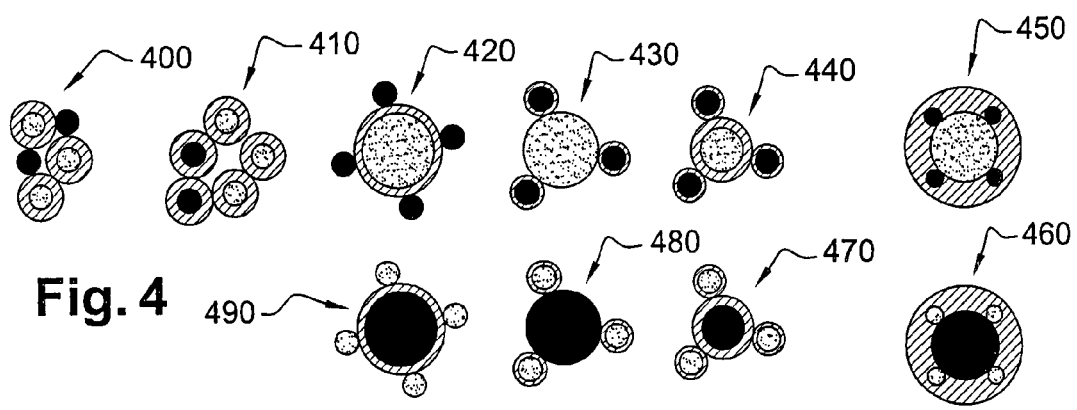
FIG. 4 is a schematic representation of a cross section of ten alternatives according to a fourth embodiment of the invention.

FIG. 4 corresponds to the fourth embodiment of the invention, in which the luminophores and/or the surface plasmon effect particles are individually covered by a separating layer made from a material transparent to infrared, visible or ultraviolet rays.

FIG. 4 thus shows ten aggregates 400, 410, 420, 430, 440, 450, 460, 470, 480 and 490 which represent as many possible combinations of their respective positions and dimensions. Thus, the separating layer may cover the particles only, as in the case of the aggregates 400, 420 and 480. The separating layer may also cover the luminophores only, as in the case of the aggregates 430 and 490. It may cover the luminophores and the particles (aggregates 410, 440 and 470). Finally, it may cover a combination similar to the aggregates 110 or 130, which is represented by the aggregates 450 and 460.

As may be further observed in FIG. 4, the relative dimensions of the particles and luminophores may vary, thereby enriching the possible combinations, and hence the luminescence spectra emitted by each of these optical coding devices.

As stated above, each separating layer, or "spacer" material, serves to maintain a controlled distance between luminophores and particles. This distance is preferably shorter than 30 nm, in order to facilitate the interactions between the luminophores and the surface plasmon effect particles.

Thus, due to these interactions, each aggregate 400, 410, 420, 430, 440, 450, 460, 470, 480, 490 emits a unique and unfalsifiable luminous spectrum.

Figure 5:
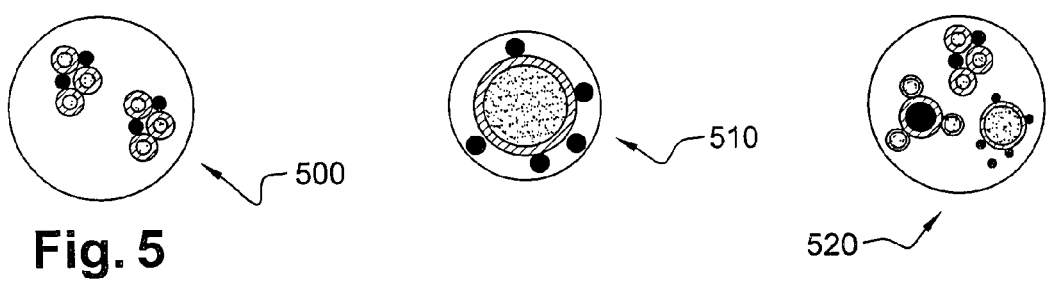
FIG. 5 is a schematic representation of a cross section of three alternatives according to a fifth embodiment of the invention.

FIG. 5 shows a number of embodiments according to the fifth embodiment of the present invention. In the present case, similar combinations to those shown in FIG. 4 are also encapsulated using an envelope transparent to infrared, visible or ultraviolet rays. Thus for example, the aggregate 500 comprises two combinations similar to the aggregate 400 formed by two luminophores and three particles covered with a separating layer.

Similarly, the aggregate 520 comprises an envelope encapsulating three combinations similar to the aggregates 400, 470 and 420. Other combinations of positions and dimensions of the various components of these aggregates are feasible while conforming to this fifth embodiment.

Figure 6:
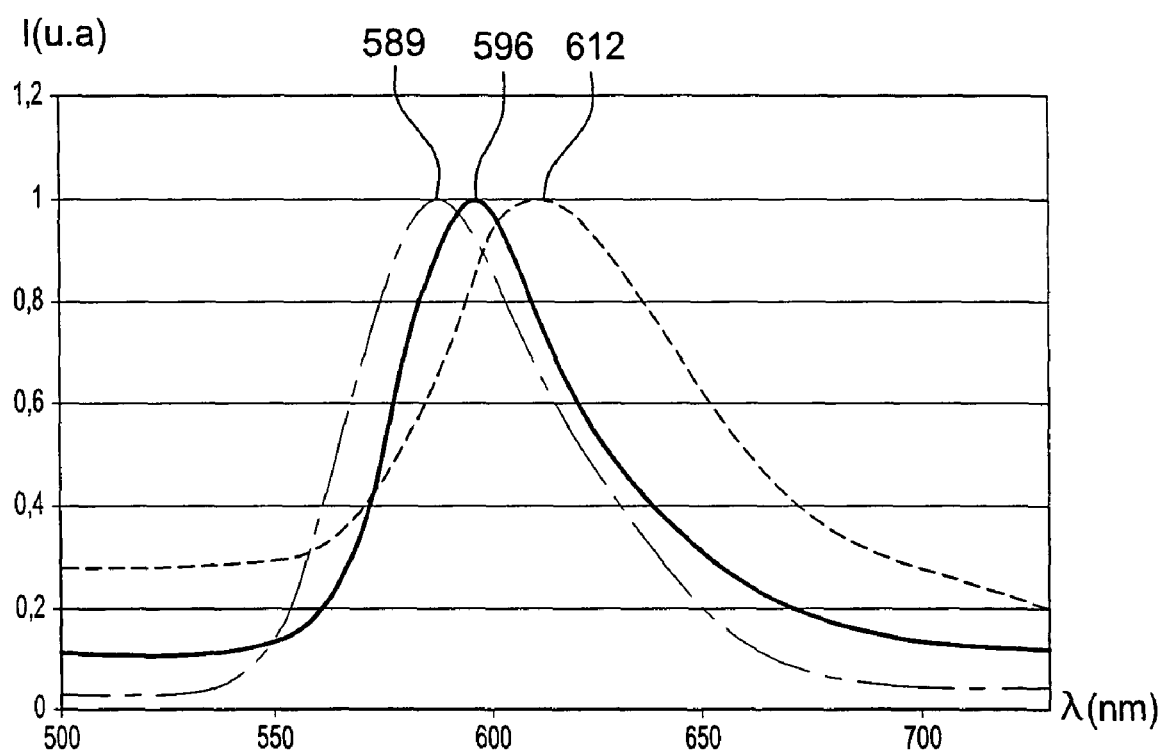
FIG. 6 is a graph showing the fluorescent spectra resulting from interactions between an organic luminophore RbITC respectively with gold nanoparticles, respectively with 8 and 16 nm in plasmon resonance, and with nanotracers without gold particles.

FIG. 6 is a graph showing the intensity of the luminous spectra as a function of the luminescence emission wavelength. This diagram reveals the influence of the surface plasmon particles interacting with luminophores.

In the present case, the luminophores consist of rhodamine-B-isothiocyanate (RBITC), while the particles consist of gold nanoparticles.

The three luminous spectra shown here correspond to the response emitted by three different samples illuminated by a light source emitting at a wavelength of 380 nm. Among these three samples, one of them is a reference sample, comprising an organic luminophore, in this case rhodamine-B-isothiocyanate (RBITC), encapsulated in a bead of polysiloxane ($SiO_2$) playing the role of an envelope. When it is illuminated by rays having a wavelength of 380 nm, this reference sample re-emits by luminescence, the luminous spectrum shown in broken lines and presenting a light intensity peak for a wavelength at 589 nm.

The other two luminous spectra correspond to samples comprising optical coding devices according to the present invention. Thus, the luminous spectrum shown by solid lines and presenting a light intensity peak for a wavelength of 596 nm derives from the luminescent emission of an optical coding device comprising aggregates comprising the same organic luminophores (RBITC) as the reference sample and gold nanoparticles constituting the surface plasmon effect particles characterizing the present invention. The aggregates of this second sample are further encapsulated, like the reference sample, in an envelope of polysiloxane ($SiO_2$).

Observation of FIG. 6 shows that the luminous spectrum emitted by the optical coding device corresponding to the second sample is shifted towards the high wavelengths. In other words, these two luminous spectra (589 and 596; broken lines and solid lines) are clearly distinct from one another.

The third luminous spectrum (612; dotted lines) represents the luminescent emission of a third sample also corresponding to an optical coding device according to the present invention. This third sample comprises similar aggregates to those comprising the second sample (596), with the only difference that the gold nanoparticles have larger dimensions. In fact, the gold nanoparticles making up the particles of the second sample (596) have a median diameter of 8 nm, while the gold nanoparticles making up the particles of the third sample have a median diameter of 16 nm.

In fact, as may be noted by observing FIG. 6, the doubling of the dimension of these particles also causes a "slippage" or shift towards the high wavelengths.

By comparison, the reference sample (589), which does not comprise surface plasmon effect particles, has a narrower spectrum centred on a lower wavelength.

Thus, the experiment illustrated by FIG. 6 clearly reveals the influence of the surface plasmons on the luminescence spectrum of the luminophores. This influence is due, as stated above, to the interactions occurring at a nanometric scale between particles and luminophores.

Thus, the optical coding device of the present invention implements specific and original physical interactions between the luminophores and the particles consisting of surface plasmon effect materials. This serves to create novel spectra signatures in luminescence, which are difficult to falsify.

For this purpose, as stated above, an optical coding device must comprise at least two different materials in mutual interaction, these two materials being positioned at a distance of a few tens of nm from one another. In fact, when the interval between the two materials increases and exceeds a certain value, there are no further interactions between particles and luminophores, so that original and therefore unique luminescence spectra are no longer obtained.

Furthermore, the optical coding devices according to the present invention must have small dimensions in order to be joinable with the object to authenticate.

These optical coding devices may be associated with all or part of the surface of this object. They may thus be located at a precise point or spread over the entire surface of this object.

It is however essential for the combination of these optical coding devices to avoid modifying the mechanical and/or aesthetic properties of the object to be authenticated. This is why it is desirable for the aggregates making up these optical coding devices to have a size lower than 200 nm. Besides, the surface plasmon effect can only be obtained with small particles, that is, having nanometric size. In consequence, the two dimensional limitations are compatible and culminate in the fabrication of nanometric optical coding devices.

Moreover, the invention has the advantage of a certain versatility of the interactions between plasmon and luminophore. Thus, by varying the size of the surface plasmon effect particles, the wavelength ranges in which these particles interfere with the luminophores can be modified, without changing the chemical nature of the materials employed. In this way, numerous optical coding devices can be fabricated each having a unique signature or luminescent spectrum. This wide variety, due to entirely different interactions, makes the falsification of the optical code virtually impossible, including by means of a chemical analysis of the materials employed.

Moreover, the interactions between luminophores and plasmon effect particles serve not only to make the intensity peak of the luminescence spectrum "slip", but also to increase or decrease the light intensity of the other parts of the spectrum, and in particular its ends, in a specific manner. This increase or decrease of light intensity also depends on the distance between the luminophore and the surface plasmon effect particle.

This is why the present invention proposes to use a separating layer and/or encapsulating envelope in order to optimise the distances between the interacting materials. As shown by FIGS. 2 to 5, numerous possibilities are available for defining a specific interval and, therefore, for preparing an optical coding device having a unique luminescence spectrum, that is an original signature.

Furthermore, the use of a separating layer and/or encapsulating envelope serves to make the aggregates making up the optical coding device more resistant to abrasion, for example.

As further shown by FIGS. 1 to 5, the present invention serves to combine a plurality of luminophores of different types or several materials of different types, for obtaining multiple interactions, which are accordingly even more complex to reproduce.

Moreover, the possibility of using particles forming an optical resonator, as stated above, in interaction with the luminophores contained in the aggregates forming the optical coding device, serves to even further extend the wavelength interval of the ranges of interference between luminophores and particles. This therefore also serves to increase the possibilities of optical coding by the creation of new luminescence spectra, while using the same base materials.

Other embodiments are feasible without necessarily going beyond the scope of the present invention.

The invention claimed is:

1. An optical coding device comprising a plurality of aggregates suitable for emitting infrared, visible or ultraviolet rays by luminescence, at least one of the aggregates comprising at least one luminophore and at least one particle consisting of a surface plasmon effect material, the luminophore and the particle being suitable for entering into interaction, wherein the aggregate comprises an envelope encapsulating the luminophore and the surface plasmon effect particle, the envelope consisting of a material transparent to infrared, visible or ultraviolet rays, wherein the presence of the surface plasmon effect particle shifts and/or broadens the optical signature of the luminophore,
wherein a separating layer surrounds the luminophore and/or the surface plasmon effect particle to distance them respectively, the separating layer consisting of a material transparent to infrared, visible or ultraviolet rays.

2. An optical coding device according to claim 1, wherein the distance between the luminophore and the surface plasmon effect particle is shorter than 30 nm.

3. An optical coding device according to claim 1, wherein the aggregate has a dimension smaller than 200 nm.

4. An optical coding device according to claim 1, wherein the particle is suitable for presenting a surface plasmon effect when it is excited by means of a spectrum having an energy entirely or partially covering the emission spectrum of the luminophore.

5. An optical coding device according to claim 4, wherein the particle comprises an electrically conducting metal having a high density and a high electronic mobility, selected from the group comprising gold, silver, copper, aluminum and sodium.

6. An optical coding device according claim 1, wherein the surface plasmon effect particle comprises a nanoparticle made from a dielectric or semiconductor material covered by an electrically conducting metal film having a high density and a high electronic mobility, selected from the group comprising gold, silver, copper, in order to form an optical resonator suitable for presenting a surface plasmon effect suitable for the luminescence spectrum of the luminophore.

7. An optical coding device according to claim 6, wherein the nanoparticle comprises a polymer or an inorganic oxide.

8. An optical coding device according to claim 7, wherein the polymer is polysiloxane.

9. An optical coding device according to claim 7, wherein the inorganic oxide is zirconium oxide or alumina.

10. An optical coding device according to claim 1, wherein the luminophore is selected from:
organic luminophores selected from the group comprising rhodamine-B-isothiocyanate (RBITC), fluorescein isothiocyanate (FITC), fluorescein, rhodamine, eosine, pyranine, aminoG;
nanocrystals of ZnO, ZnS, CdSe, InGaP, InP, Si, Ge, GaAs, GaP, GaAsP;
oxide, sulphide, phosphate or vanadate matrices doped with a rare earth ion, such as $Y_2O_3$:Eu, $Y_2O_2S$:Eu, $BaMgAl_{16}O_{17}$:Eu, $GdBO_3$:Eu, $YGdBO_3$:Eu, $YPVO_4$:Eu, $Gd_2O_3$:Tb, $Gd_2O_2S$:Tb, $Y_3Al_5O_{12}$:Tb, $Y_2SiO_5$:Ce, $LaPO_4$:Tb, Ce;
semiconductor or oxide matrices doped with a transition metal, such as ZnS:Mn, ZnS:Au, ZnS:Al, ZnS:Ag, ZnO:Ag, ZnO:Cu, ZnO:Mn, $Zn_2SiO_4$:Mn, $Al_2O_3$:Cr, $Al_2O_3$:Ti.

11. An optical coding device according to claim 1, wherein the separating layer consists of a polymer or an inorganic oxide.

12. An optical coding device according to claim 11, wherein the polymer is polysiloxane.

13. An optical coding device according to claim 11, wherein the inorganic oxide is zirconium oxide or alumina.

14. An optical coding device according to claim 1, wherein the envelope consists of one of polysiloxane, zirconium oxide or alumina.

15. An optical coding device according to claim 1, wherein the peak wavelength of the optical signature is shifted without an increase in intensity of the peak.

16. A method of shifting and/or broadening the optical signature of a luminophore by forming an aggregate comprising at least one luminophore and at least one particle consisting of a surface plasmon effect material, and encapsulating the luminophore and the surface plasmon effect particle in an envelope consisting of a material that is transparent to infrared, visible or ultraviolet rays, wherein the material of the surface plasmon effect particle is selected and the position of the surface plasmon effect particle relative to the luminophore is predetermined by a separating layer that surrounds the luminophore and/or the surface plasmon effect particle to distance them respectively, the separating layer consisting of a material that is transparent to infrared, visible or ultraviolet rays, to shift and/or broaden the optical signature of the luminophore.

17. A method of shifting and/or broadening the optical signature of a luminophore according to claim 16, wherein the peak wavelength of the optical signature is shifted without an increase in intensity of the peak.

18. A method for marking textile, paper, glass or plastic, comprising joining to said textile, paper, glass or plastic an optical coding device comprising a plurality of aggregates suitable for emitting infrared, visible or ultraviolet rays by luminescence, at least one of the aggregates comprising at least one luminophore and at least one particle consisting of a surface plasmon effect material, the luminophore and the particle being suitable for entering into interaction, wherein the aggregate comprises an envelope encapsulating the luminophore and the surface plasmon effect particle, the envelope consisting of a material transparent to infrared, visible or ultraviolet rays, wherein the presence of the surface plasmon effect particle shifts and/or broadens the optical signature of the luminophore,
wherein a separating layer surrounds the luminophore and/or the surface plasmon effect particle to distance them respectively, the separating layer consisting of a material transparent to infrared, visible or ultraviolet rays.

19. A method of marking textile, paper, glass or plastic according to claim 18, wherein the peak wavelength of the optical signature is shifted without an increase in intensity of the peak.

20. A method for authenticating textile, paper, glass or plastic, comprising:

integrating an optical coding device with said textile, paper, glass or plastic, said optical coding device comprising a plurality of aggregates suitable for emitting infrared, visible or ultraviolet rays by luminescence, at least one of the aggregates comprising at least one luminophore and at least one particle consisting of a surface plasmon effect material, the luminophore and the particle being suitable for entering into interaction, wherein the aggregate comprises an envelope encapsulating the luminophore and the surface plasmon effect particle, the envelope consisting of a material transparent to infrared, visible or ultraviolet rays, wherein the presence of the surface plasmon effect particle shifts and/or broadens the optical signature of the luminophore, wherein a separating layer surrounds the luminophore and/or the surface plasmon effect particle to distance them respectively, the separating layer consisting of a material transparent to infrared, visible or ultraviolet rays;

illuminating said textile, paper, glass or plastic using a light source emitting infrared, visible or ultraviolet rays;

sensing the rays re-emitted by said textile, paper, glass or plastic using a spectral detector;

comparing the luminous spectrum emitted by said textile, paper, glass or plastic to a reference spectrum;

declaring the authenticity or inauthenticity of said textile, paper, glass or plastic.

21. A method of authenticating textile, paper, glass or plastic according to claim 20, wherein the peak wavelength of the optical signature is shifted without an increase in intensity of the peak.

* * * * *